United States Patent [19]

Liang et al.

[11] Patent Number: 5,872,161
[45] Date of Patent: Feb. 16, 1999

[54] DENTURE ADHESIVE COMPOSITIONS

[75] Inventors: Nong Liang, West Chester; Jayanth Rajaiah, Loveland, both of Ohio

[73] Assignee: The Procter & Gamble Company, Cincinnati, Ohio

[21] Appl. No.: 835,041

[22] Filed: Mar. 27, 1997

[51] Int. Cl.⁶ .............................. A61K 6/00; A61C 13/23; C09J 7/00
[52] U.S. Cl. ............................................................ 523/120
[58] Field of Search .............................................. 523/120

[56] References Cited

U.S. PATENT DOCUMENTS

| | | | |
|---|---|---|---|
| 1,917,902 | 7/1933 | Rowe . | |
| 2,897,593 | 8/1959 | Hollander et al. | 32/2 |
| 3,575,915 | 4/1971 | Novak et al. | 260/29.6 |
| 3,736,274 | 5/1973 | Schoenholz et al. | 260/17 R |
| 3,990,149 | 11/1976 | Nedwig | 32/2 |
| 4,136,163 | 1/1979 | Watson et al. | 424/54 |
| 4,202,098 | 5/1980 | Russo | 433/168 |
| 4,373,036 | 2/1983 | Chang et al. | 523/120 |
| 4,503,116 | 3/1985 | Lapidus | 428/286 |
| 4,529,748 | 7/1985 | Wienecke | 523/120 |
| 4,632,880 | 12/1986 | Lapidus | 428/523 |
| 4,758,630 | 7/1988 | Shah et al. | 523/120 |
| 4,772,470 | 9/1988 | Inoue et al. | 424/435 |
| 4,880,702 | 11/1989 | Homan et al. | 428/354 |
| 4,910,247 | 3/1990 | Haldar et al. | 523/120 |
| 5,006,571 | 4/1991 | Kumar et al. | 523/120 |
| 5,073,604 | 12/1991 | Holeva et al. | 523/120 |
| 5,093,387 | 3/1992 | Schobel et al. | 523/120 |
| 5,158,825 | 10/1992 | Altwirth | 428/286 |
| 5,166,233 | 11/1992 | Kuroya et al. | 524/37 |
| 5,204,414 | 4/1993 | Pelah et al. | 525/327.8 |
| 5,209,777 | 5/1993 | Altwirth | 106/35 |
| 5,298,534 | 3/1994 | Prosise et al. | 523/120 |
| 5,304,616 | 4/1994 | Rajaiah et al. | 526/240 |
| 5,369,145 | 11/1994 | Gasman et al. | 523/120 |
| 5,395,867 | 3/1995 | Prosise et al. | 523/120 |
| 5,424,058 | 6/1995 | Rajaiah et al. | 523/120 |
| 5,525,652 | 6/1996 | Clarke et al. | 524/37 |
| 5,543,443 | 8/1996 | Rajaiah et al. | 523/120 |
| 5,624,745 | 4/1997 | Lapidus | 428/308.8 |
| 5,635,568 | 6/1997 | Plochocka et al. | 525/362 |
| 5,658,586 | 8/1997 | Rajaiah et al. | 424/435 |

FOREIGN PATENT DOCUMENTS

| | | | |
|---|---|---|---|
| 0353375 | 2/1990 | European Pat. Off. | A61C 13/23 |
| 0555019 A1 | 8/1993 | European Pat. Off. | A61K 6/00 |
| 3613432 | 10/1987 | Germany | A61C 13/23 |
| 59-110616 | 6/1984 | Japan | A61K 9/70 |
| 63-54318 | 3/1988 | Japan | A61K 9/70 |
| 4-149110 | 5/1992 | Japan . | |
| 5-65210 | 3/1993 | Japan . | |
| 5-65211 | 3/1993 | Japan . | |
| WO 96/04883 | 2/1996 | WIPO | A61K 6/87 |

*Primary Examiner*—Shep K. Rose
*Attorney, Agent, or Firm*—Betty J. Zea; Mary Catherine Hentz; Jacobus C. Rasser

[57] ABSTRACT

Disclosed is a denture adhesive composition comprising a partial salt of a lower alkyl vinyl ether-maleic acid copolymer wherein the partial salt comprises a cationic salt function consisting essentially of: from about 0.01% to about 10% of ferric iron cations; and from about 0.1% to about 75% of divalent and/or monovalent metal cations selected from the group consisting of zinc, calcium, magnesium, potassium, sodium, ammonium, and mixtures thereof.

17 Claims, No Drawings

DENTURE ADHESIVE COMPOSITIONS

BACKGROUND OF THE INVENTION

Ordinary removable dentures, dental plates and the like, comprise teeth mounted in a suitable plate or base. Denture adhesives or stabilizers are used to provide a cushion or gasket between the denture and the gums or tissues and to fill the interstices between the dentures and the gums or tissues.

Denture stabilizing or adhesive compositions can exhibit several deficiencies. Aesthetic deficiencies may include oozing of the adhesive from under the dental plate during insertion and throughout the wearing period and messiness and difficulty of removing the residual adhesive from the mouth and dentures. Additionally, food may become trapped between the denture and the oral cavity of the wearer. Considerable effort has been made over the years to develop denture adhesive compositions with improved holding capabilities which are aesthetically pleasing and easy to use. Both synthetic and natural polymers and gums have been used singly, in combination, and in combination with various adhesives and other materials in an attempt to lessen the deficiencies commonly associated with denture adhesive products.

Lower alkyl vinyl ether-maleic copolymers and salts thereof are known in the art for use in denture adhesive compositions. Such disclosures include: U.S. Pat. No. 3,003,988 to German et al., issued Oct. 10, 1961; U.S. Pat. No. 4,980,391 to Kumar et al., issued Dec. 25, 1990; U.S. Pat. No. 5,073,604 to Holeva et al., issued Dec. 17, 1991; and U.S. Pat. No. 5,525,652 to Clarke, issued Jun. 11, 1996. Despite the above-noted technologies, as well as others, a need still exists for denture stabilizing compositions providing improved hold and aethestics.

In accordance with the present invention, it has been discovered that denture adhesive compositions comprising ferric iron and divalent and/or monovalent metal partial salts of lower alkyl vinyl ether-maleic acid copolymers provide superior denture stability and retention over a significantly longer period of time versus conventional denture adhesives. Specifically, the compositions exhibit higher resistance to salivary washout while maintaining the same or better denture hold as conventional denture adhesives. This added resistance to salivary washout translates to longer denture hold and stability.

Therefore, it is an object of the present invention to provide ferric iron and divalent and/or monovalent metal partial salts of lower alkyl vinyl ether-maleic copolymers. It is also an object of the invention to provide improved adhesive compositions which may be used with dentures and to provide a firm hold and exhibit higher resistance to salivary washout.

These and other objects of the present invention will become readily apparent from the detailed description which follows.

SUMMARY OF THE INVENTION

The present invention relates to a denture adhesive composition comprising partial salts of a lower alkyl vinyl ether-maleic acid copolymer wherein the partial salt contains a cationic salt function consisting essentially of from about 0.1% to about 10% ferric iron cations; and from about 0.1% to about 75% of divalent and/or monovalent metal cations selected from the group consisting of zinc, calcium, magnesium, potassium, sodium, ammonium, and mixtures thereof.

DETAILED DESCRIPTION OF THE INVENTION

The denture adhesive compositions of the present invention comprise a partial salt of a lower alkyl vinyl ether-maleic acid copolymer having a cationic salt function consisting essentially of ferric iron cations and also one or more of divalent and/or monovalent metal cations. The adhesive compositions may in the form of a powder which is sprinkled on a dental prosthesis, moistened and then inserted into the oral cavity. The compositions may also be combined with various conventional delivery vehicles to form liquids or pastes which are applied to a dental prosthesis and inserted into the oral cavity. A detailed description of essential and optional components of the present invention is given below.

Lower Alkyl Vinyl Ether-Maleic Partial Salt Polymer

The lower alkyl vinyl ether-maleic acid ("AVE/MA") copolymer consists essentially of the repeated structural unit:

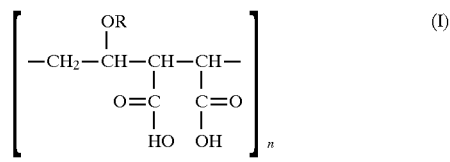

wherein R represents a C1 to C4 alkyl radical, n is an integer greater than one representing the number of repeated occurrences of the structural unit in a molecule of the copolymer. In characterizing the copolymer, n is large enough such that the specific viscosity of the copolymer is larger than 1.2, the specific viscosity being determined in methyl ether ketone at 25° C.

Lower alkyl vinyl ether maleic polymers are readily obtained by copolymerizing a lower alkyl vinyl ether monomer, such as methyl vinyl ether, ethyl vinyl ether, divinyl ether, propyl vinyl ether, isobutyl vinyl ether and the like, with maleic anhydride to yield the corresponding lower alkyl vinyl ether-maleic anhydride copolymer which is readily hydrolyzable to the acid copolymer. In general, the resulting copolymer is a 1:1 copolymer. Both anhydride and acid forms are also available from commercial suppliers. For example, ISP Technologies Inc. ("ISP"), Wayne, N.J., provides both the polymeric free acid form (I) and the corresponding anhydride form under its "GANTREZ" trademark as the "GANTREZ S Series" and "GANTREZ AN Series", respectively. In the former acid series, the GANTREZ S-97 is particularly suitable, and, in the latter anhydride series, the GANTREZ AN-149 (specific viscosity of 1.5 to 2.5) the GANTREZ AN-169 (specific viscosity of 2.6 to 3.5) and the GANTREZ AN-179 (specific viscosity of 3.5 to 5.0) copolymers are particularly suitable. These copolymers are described in greater detail in U.S. Pat. No. 5,395,867 to Prosise, issued Mar. 7, 1995; which is incorporate herein by reference in its entirety. When the anhydride copolymer dissolves in water, the anhydride linkage is cleaved so that the highly polar, polymeric free acid (I) is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

The lower alkyl vinyl ether-maleic acid ("AVE/MA") polymers useful in the present invention are partial copolymer salts. Such salts comprise a cationic salt function. The cationic salt function contains ferric iron and also one or more metal cations selected from the group consisting of divalent cations, monovalent cations, and mixtures thereof. Divalent metal cations include zinc, strontium (but not used in combination with zinc), calcium, magnesium and mixtures thereof. Monovalent metal cations include sodium, potassium, ammonium, and mixtures thereof. Partial salts of lower alkyl vinyl ether-maleic acid polymers are also described in U.S. Pat. No. 5,073,604 to Holeva et al., issued Dec. 17, 1991; U.S. Pat. No. 5,204,414 to Pelah et al., issued Apr. 20, 1993; and U.S. Pat. No. 5,525,652 to Clarke, issued Jun. 11, 1996; all of which are incorporated herein by reference.

The copolymer salts may be mixed or unmixed or both. The term "unmixed polymer salts" as used herein refers to salts of lower alkyl vinyl ether-maleic polymers wherein the cations are unmixed with any other ester functions or nonidentical cations on the same polymer, the remaining carboxyl groups being unreacted.

The term "mixed polymer salts" as used herein refers to salts of the lower alkyl vinyl ether-maleic polymers where different cations are mixed on the same polymer with each other or with other ester functions. Preferred are mixed polymer salts containing zinc and calcium cations.

Partial copolymer salts comprising ferric iron cations can be prepared by the interaction of the AVE/M anhydride/acid copolymers with ferric compounds, in the form of a salt, such as ferric sulfate pentahydrate. Partial copolymer salts comprising divalent and/or monovalent metal cations can be prepared by the interaction of the AVE/M anhydride/acid copolymers with metal cation (such as zinc, strontium, calcium, magnesium, sodium, potassium, or ammonium) compounds either in the form of a base or a salt; such as, for example, the hydroxide, acetate, halide, lactate, etc. in an aqueous medium. In a preferred embodiment, the oxide of zinc and the hydroxide of calcium are utilized. Since zinc hydroxide is not commercially available, its use as a reactant is readily and more economically accomplished by employing an aqueous slurry of particular zinc oxide which, although practically insoluble in water, provides hydration to zinc hydroxide on the particulate surface.

The sum total of the metal cations in the resultant partial salt of AVE/MA copolymers should be sufficient to give a neutralization ranging from about 0.1% to about 75% of divalent and/or monovalent metal cations, of the initial carboyxl groups reacted. The resulting partial salt copolymer contains free acid in the range of from about 5% to about 50%.

In preferred partial copolymer salts, the cationic salt function contains ferric iron from about 0.01% to about 10%, preferably from about 0.05% to about 5%, and most preferably from about 0.1% to about 3%, of the initial carboxyl groups reacted; zinc from about 10% to about 65%, preferably from about 5% to about 45%, and most preferably from about 10% to about 30%, of the initial carboxyl groups reacted; and calcium from about 10% to about 75%, preferably from about 25% to about 60%, and most preferably from about 40% to about 60%, of the total initial carboxyl groups reacted. Also preferred is sodium from about 1% to about 20%, preferably from about 1% to about 15%, and most preferably from about 1% to about 10%, of the total initial carboxyl groups reacted; and strontium from about 10% to about 75%, preferably from about 25% to about 60%, and most preferably from about 40% to about 60%, of the total initial carboxyl groups reacted.

Cations that form toxic, irritating or contaminating by-products should be avoided, or special precautions and treatment provided to assure the removal and absence of such by-products from the polymeric salt end-product. The particular compound used should be substantially pure to assure obtaining a substantially pure, substantially off-white copolymeric salt end-product. The partial salt copolymers are utilized in the present composition in an amount of at least 10 percent and more preferably in amount of at least 20 percent, by weight of the adhesive composition.

Reducing Agent

The present invention can also comprise the use of a reducing agent. The reducing agent aids in removal of the denture from the oral cavity after application of the present ferric iron/divalent and/or monovalent metal cation partial copolymer salts to the denture. While not to be bound by theory, it is believed that the reducing agent reduces ferric iron to ferrous iron, thus reducing the adhesive properties of the partial salt copolymer and facilitating removal of the denture(s). The preferred reducing agent for use herein is ascorbic acid and its water soluble salts.

The reducing agent may also be used in combination with a chelating agent. Preferred chelating agents include citrate, tartrate, lactate, and the like. The reducing agent and/or chelating agent may also be delivered in a composition by carriers known in the art which are safe for oral administration (i.e., non-toxic and approved for use in humans). Such carriers include surfactants, and solvents.

The reducing agent and/or chelating agents are used in safe and effect amounts. The term "safe and effective amount", as used herein, means an amount sufficient to aid in releasing the denture hold in the oral cavity without toxicity to the user, damage to oral tissue, and alteration of the denture material. Thus, a denture wearer applies the ferric iron/metal(s) cation partial copolymer salt adhesive composition to dentures and inserts them into the oral cavity. When removal is desired, the wearer swishes in the mouth, a denture releasing composition comprising a reducing agent and/or chelating agents and suitable solvent(s) which aids in releasing the denture hold.

Additional Adhesive Components

The present invention compositions may also include other adhesive components. These adhesive components, if present, are used in safe and adhesively effective amounts. The term "safe and adhesively effective amount" as used herein means an amount sufficient to provide adherence of a dental prosthesis to the palate and ridge of the oral cavity without toxicity to the user, damage to oral tissue, and alteration of the denture material.

Suitable adhesive components include a water-soluble hydrophilic colloid or polymer having the property of swelling upon exposure to moisture to form a mucilaginous mass. Such adhesive materials include natural gums, synthetic polymeric gums, adhesive materials commonly employed in denture stabilizing compositions and compatible with the subject AVE/MA copolymers, synthetic polymers, mucoadhesive polymers, hydrophilic polymers, saccharide derivatives, cellulose derivatives, and mixtures thereof. Examples of such materials include karaya gum, guar gum, gelatin, algin, sodium alginate, tragacanth, chitosan, polyethylene glycol, acrylamide polymers, carbopol, polyvinyl alcohol, polyamines, polyquarternary compounds, polybutenes, silicones, ethylene oxide polymers, polyvinylpyrrolidone, cationic polyacrylamide polymers.

Preferred are cellulose derivatives such as methylcellulose, sodium carboxymethylcellulose, hydroxyethylcellulose, hydroxypropylcellulose, hydroxypropylmethylcellulose, carboxymethylcellulose. Most preferred are carboxymethylcellulose, polyethylene glycol, polyethylene oxide, karaya gum, sodium alginate, chitosan, polyvinyl alcohol, and mixtures thereof. In general, the other adhesive components may be present at a level of from about 0% to about 70%, preferably from about 10% to about 50%, and most preferably from about 20% to about 40%, by weight of the composition.

Other Ingredients

One or more toxicologically-acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 70%, preferably from about 0.1% to about 30%, by weight of the composition.

The denture adhesive compositions may also be used as a denture adhesive and/or bioadhesive and comprise one or more therapeutic actives suitable for mucosal or topical administration. The phrase "suitable for mucosal or topical administration", as used herein, describes agents which are pharmacologically active when absorbed through internal mucosal surfaces of the body such as the oral cavity, or applied to the surfaces of the skin. Therapeutic actives may be present at a level of from about 0% to about 70%, by weight of the composition.

Therapeutic actives that are useful in these compositions include antimicrobial agents such as iodine, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, cimetidine, eugenol, or hydrocortisone; dentinal desensitizing agents such as potassium nitrate, strontium chloride or sodium fluoride; anesthetic agents such as lidocaine or benzocaine; anti-fungals; aromatics such as camphor, eucalyptus oil, and aldehyde derivatives such as benzaldehyde; insulin; steroids; and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Other suitable ingredients include silicon dioxide, colorants, preservatives such as methyl and propyl parabens; thickeners, and polyethylene glycol; and delivery vehicles such as liquid petrolatum, petrolatum, mineral oil and glycerin. Preferred are polyethylene glycol, silicon dioxide, and petrolatum. Colorants, preservatives, thickeners and delivery vehicles may be present at levels of from about 0% to about 20%, by weight of the composition.

The compositions of the present invention may also include one or more components which provide flavor, fragrance, and/or sensate benefit. Suitable components include natural or artificial sweetening agents, menthol, menthyl lactate, wintergreen oil, peppermint oil, spearmint oil, leaf alcohol, as well as coolants 3-1-menthoxypropane-1,2-diol and paramenthane carboxyamide agents such as N-ethyl-p-menthane-3-carboxamide which is described in U.S. Pat. No. 4,136,163 to Watson et. al., which is incorporated by reference herein in its entirety. These agents may be present at a level of from about 0% to about 50%, by weight of the composition.

Process for Preparation of the Composition

The present adhesive copolymers can be prepared by any of the methods or combination of methods which follow. The lower alkyl vinyl ether maleic anhydride copolymers can be obtained either from commercial suppliers under the trade names disclosed previously or by copolymerization of a lower alkyl vinyl ether monomer with maleic anhydride to yield the corresponding lower alkyl vinyl ether-maleic anhydride copolymer which is readily hydrolyzable to the acid copolymer. Processes for the preparation of partial AVE/MA copolymer salts is also described in U.S. Pat. No. 5,073,604 to Holeva, issued Dec. 17, 1991, (previously incorporated by reference herein).

The AVE/MA copolymer is hydrolyzed and neutralized in an aqueous mixture or slurry of one or more divalent and/or monovalent metal bases by heating the copolymer/base mixture to a temperature ranging from about 45° C. to about 100° C. Reaction of the partial AVE/MA copolymer salt with ferric iron cations is obtained through addition of ferric iron salts to the hydrolyzed and neutralized partial salt of the AVE/MA copolymer. Completion of the reaction with ferric iron cations is indicated by an increase in viscosity to stabilization. Alternatively, ferric iron salts may be blended with the copolymer/metal base mixture prior to the hydrolysis and neutralization reactions.

The resulting slurry or solution is transferred to shallow stainless steel drying trays and placed in a forced air mechanical convection oven at 60° C. for a time sufficient to evaporate the reaction medium (water) and remove water from the copolymer (about 18–24 hours). Alternatively, the resulting slurry or solution can be drum-dried. After drying, the polymer forms brittle flakes which can easily be peeled off from the trays or drum surface and ground to a fine powder as desired.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLE I

Into a 2 liter resin reaction kettle, equipped with a high torque mixer with a built-in viscosity monitor, which contains 1484.95 grams of purified water, USP at room temperature, add 0.048 grams of ferric sulfate pentahydrate ($Fe_2(SO_4)_3 \bullet 5H_2O$). Mix for about 5 minutes at 300 rpm with a paddle stirring element. Slowly add 15.00 grams of 65% neutralized mixed calcium (47.5%) and zinc (17.5%) partial salt of methyl vinyl ether/maleic acid ("MVE/MA") copolymer made from Gantrez® AN169 at an appropriate speed such that the salt is dispersed before it becomes fully hydrated. Heat the resin reaction kettle with a temperature controlled water bath to 90° C. and maintain the reaction temperature between 85° C. and 95° C. at a constant agitation rate of 300 rpm until no clumps are visible (1 to 3 hours). The reaction batch is a homogeneous dispersion of water insoluble polymer.

Transfer the resulting slurry to shallow stainless steel drying trays. Dry in a forced air mechanical convection oven at 60° C. for a sufficient time to evaporate the reaction medium (water) and remove the water from the polymer (about 18 to 24 hours). After drying, the sticky polymer forms brittle flakes easily peeling off from the drying trays. Grind the flakes to a fine powder in a milling apparatus such as speed-rotor mill with an appropriate screen to define the mean particle size and its distribution. A 0.12 mm or 0.08 mm screen is preferred. The resulting adhesive copolymer yields a 65% neutralized [mixed calcium (47.5%), zinc (17.5%)] and ferric iron (0.4%) partial salt of MVE/MA copolymer.

Variations in the amount of ferric iron useful herein include the following:

|   | $Fe_2(SO_4)_3 \cdot 5H_2O$ (gram) | Fe(III)% |
|---|---|---|
| A | 0.024 | 0.2 |
| B | 0.048 | 0.4 |
| C | 0.072 | 0.6 |
| D | 0.096 | 0.8 |
| E | 0.120 | 1.0 |

EXAMPLE II

Into a 2 liter resin reaction kettle, equipped with a high torque mixer with a built-in viscosity monitor, which contains 1429.50 grams of purified water, USP at room temperature, add 0.60 grams of ferric sulfate pentahydrate $(Fe_2(SO_4)_3 \bullet 5H_2O)$. Mix for about 5 minutes at 300 rpm with a paddle stirring element. Slowly add 12.30 grams of calcium hydroxide until the solid is well dispersed. Then slowly add 57.60 grams of MVE/MA copolymer or Gantrez® AN169 until the solid is well dispersed. Heat the resin reaction kettle with a temperature controlled water bath to 90° C. and maintain the reaction temperature between 85° C. and 95° C. at a constant agitation rate of 300 rpm. Transparent clarity of the reaction batch and an increase in pH to a stable value, (typically around pH 4.9 measured in an aliquot of 1:10 (v/v) dilution) indicates the completion of hydrolysis and neutralization reactions.

Repeat the drying and milling procedures described in Example I. The resulting adhesive copolymer yields a 45% neutralized [Ca (45%)] and Fe(III) (1.0%) partial salt of MVE/MA copolymer.

EXAMPLE III

Denture stabilizing compositions in powder form can be made by blending together the following ingredients:

|   |   | % w/w |
|---|---|---|
| A | Carboxymethylcellulose Sodium | 58.9 |
|   | 47.5% Ca, 17.5% Zn, 0.4% Fe(III) Partial Salt of MVE/MA Copolymer | 40.0 |
|   | Silicon Dioxide, Colloidal | 1.0 |
|   | Peppermint Flavor Oil | 0.1 |
| B | Karaya Gum | 40.0 |
|   | Carboxymethylcellulose Sodium | 28.9 |
|   | 47.5% Ca, 17.5% Zn, 0.4% Fe(III) Partial Salt of MVE/MA Copolymer | 30.0 |
|   | Silicon Dioxide, Colloidal | 1.0 |
|   | Peppermint Flavor Oil | 0.1 |
| C | Carboxymethylcellulose Sodium | 50.0 |
|   | 45.0% Ca, 1.0% Fe(III) Partial Salt of MVE/MA Copolymer | 48.9 |
|   | Silicon Dioxide, Colloidal | 1.0 |
|   | Peppermint Flavor Oil | 0.1 |

EXAMPLE IV

Denture stabilizing compositions in cream form can be made by blending together the following ingredients:

|   | A %, w/w | B %, w/w | C % w/w |
|---|---|---|---|
| White Mineral Oil | 24.82 | 24.82 | 24.82 |
| Petrolatum | 19.02 | 19.02 | 19.08 |
| Carboxymethylcellulose Sodium | 22.00 | 32.00 | 12.00 |
| Silicon Dioxide, Colloidal | 1.10 | 1.10 | 1.10 |
| Colorant (oil soluble red color dispersion) | 0.06 | 0.06 | — |
| 47.5% Ca, 17.5% Zn, 0.4% Fe(III) Partial Salt of MVE/MA Copolymer | 33 | — | — |
| 27.5% Ca, 20.0% Sr, 17.5% Zn, 0.5% Fe(III) Partial Salt of MVE/MA Copolymer | — | 23 | — |
| 45.0% Ca, 1.0% Fe(III) Partial Salt of MVE/M Copolymer | — | — | 43 |

Flavor oil may be incorporated into the composition at 0.1% to 0.5% (w/w) level.

EXAMPLE V

Denture stabilizing compositions in liquid form can be made by blending together the following ingredients:

|   | A %, w/w | B %, w/w | C % w/w |
|---|---|---|---|
| White Mineral Oil | 48.82 | 50.82 | 46.88 |
| Petrolatum | 5.02 | 3.02 | 7.02 |
| Carboxymethylcellulose Sodium | 18.00 | 26.00 | 8.00 |
| Silicon Dioxide, Colloidal | 1.10 | 1.10 | 1.10 |
| Colorant (oil soluble red color dispersion) | 0.06 | 0.06 | — |
| 47.5% Ca, 17.5% Zn, 0.4% Fe(III) Partial Salt of MVE/MA Copolymer | 27 | — | — |
| 27.5% Ca, 20.0% Sr, 17.5% Zn, 0.5% Fe(III) Partial Salt of MVE/MA Copolymer | — | 19. | — |
| 45.0% Ca, 1.0% Fe(III) Partial Salt of MVE/MA Copolymer | — | — | 37 |

Flavor oil may be incorporated into the composition at 0.1% to 0.5% (w/w) level.

What is claimed is:

1. A denture adhesive composition comprising a partial salt of a lower alkyl vinyl ether-maleic acid copolymer wherein the partial salt comprises a cationic salt function consisting essentially of:

(a) from about 0.01% to about 10% of ferric iron cations; and (b) from about 0.1% to about 75% of divalent or monovalent metal cations selected from the group consisting of zinc, calcium, strontium, magnesium, potassium, sodium, ammonium, and mixtures thereof;

wherein strontium cations are not used in combination with zinc cations.

2. A denture adhesive composition comprising a partial salt of a lower alkyl vinyl ether-maleic acid copolymer wherein the partial salt comprises a cationic salt function consisting essentially of:

(a) from about 0.05% to about 5% of ferric iron cations; and (b) from about 0.1% to about 75% of divalent or monovalent metal cations selected from the group consisting of zinc, calcium, strontium, magnesium, potassium, sodium, ammonium, and mixtures thereof;

wherein strontium cations are not used in combination with zinc cations.

3. A denture adhesive composition comprising from about 10% to about 50% carboxymethylcellulose, by weight of the composition, and a partial salt of a lower alkyl vinyl ether-maleic acid copolymer wherein the partial salt comprises a cationic salt function consisting essentially of:

(a) from about 0.1% to about 3% of ferric iron cations; and (b) from about 10% to about 65% of zinc, of the initial carboxyl groups reacted, and from about 10% to about 75% calcium, of the initial carboxyl groups reacted;

wherein strontium cations are not used in combination with zinc cations.

4. A method of aiding the removal of a denture from the oral cavity after the application of the composition of claim 1 to the denture by applying to the oral cavity, a denture releasing composition comprising a safe and effective amount of a reducing agent and optionally a safe and effective amount of a chelating agent.

5. A method of aiding the removal of a denture from the oral cavity after the application of the composition of claim 2 to the denture by applying to the oral cavity, a denture releasing composition comprising a safe and effective amount of a reducing agent and optionally a safe and effective amount of a chelating agent.

6. A method of aiding the removal of a denture from the oral cavity after the application of the composition of claim 3 to the denture by applying to the oral cavity, a denture releasing composition comprising a safe and effective amount of a reducing agent and optionally a safe and effective amount of a chelating agent.

7. The denture adhesive composition according to claim 1 wherein the metal cations are divalent metal cations selected from the group consisting of zinc, calcium, magnesium and mixtures thereof.

8. The denture adhesive composition according to claim 1 further comprising one or more ingredients selected from the group consisting of additional adhesive components, plasticizers, colorants, preservatives, thickeners, delivery vehicles, flavors, fragrances, sensates, and mixtures thereof.

9. The denture adhesive composition according to claim 2 comprising from about 0.1% to about 3% ferric iron cations.

10. The denture adhesive composition according to claim 5 further comprising an additional adhesive component selected from the group consisting of natural gums, synthetic polymers, mucoadhesive polymers, hydrophilic polymers, natural polymers, saccharide derivatives, cellulose derivatives, and mixtures thereof.

11. The denture adhesive composition according to claim 10 wherein the cellulose derivatives are selected from the group consisting of hydroxyethylcellulose, hydroxypropylcellulose, hydroxypropylmethylcellulose, sodium carboxymethylcellulose, and mixtures thereof.

12. The denture adhesive composition according to claim 11 further comprising a toxicologically-acceptable plasticizer.

13. The denture adhesive composition according to claim 12 wherein the plasticizer is selected from the group consisting of dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene ethyl sulfonamide, and mixtures thereof.

14. The denture adhesive composition according to claim 13 further comprising one or more ingredients selected from the group consisting of colorants, preservatives, thickeners, delivery vehicles, flavors, fragrances, sensates, and mixtures thereof.

15. The denture adhesive composition according to claim 14 wherein the flavors, fragrances, and sensates are selected from the group consisting of natural or artificial sweeteners, menthol, menthyl lactate, wintergreen oil, 3-1-menthoxypropane-1,2-diol, peppermint oil, spearmint oil, leaf alcohol, paramenthane caboxyamides, and mixtures thereof.

16. The denture adhesive composition according to claim 6 further comprising one or more ingredients selected from the group consisting of plasticizers, colorants, preservatives, thickeners, delivery vehicles, flavors, fragrances, sensates, and mixtures thereof.

17. A process for the preparation of the denture adhesive composition according to claim 1 comprising the steps of:

a) partially neutralizing a lower alkyl vinyl ether-maleic acid copolymer with one or more metal cations selected from the group consisting of divalent metal cations, monovalent metal cations, and mixtures thereof;

b) adding ferric iron cations to the partially neutralized copolymer to form a partial copolymer salt composition; and c) drying the composition to form a powder.

* * * * *